Sept. 9, 1958 W. FLEMER III Plant Pat. 1,748
MAPLE TREE
Filed Jan. 30, 1958
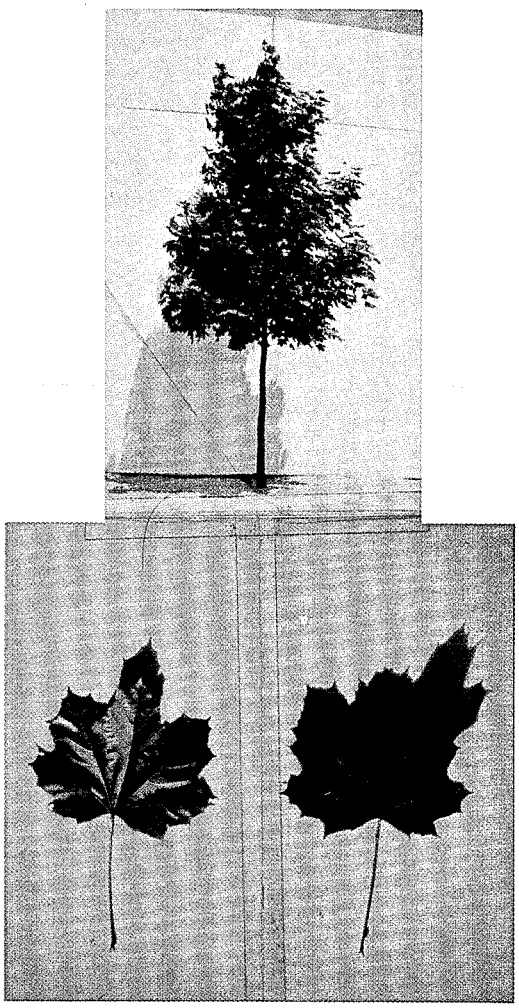
INVENTOR
William Flemer, III
BY Robb & Robb
ATTORNEYS United States Patent Office Plant Pat. 1,748
Patented Sept. 9, 1958

1,748

MAPLE TREE

William Flemer III, Princeton, N. J., assignor to Princeton Nurserymen's Research Associates, Kingston, N. J., a partnership Application January 30, 1958, Serial No. 712,288

1 Claim. (Cl. 47—59)

The present invention relates to a new and distinct variety of Norway maple tree which originated from seeds collected by me from an unpatented columnar Norway maple tree botanically known as *"Acer platanoides erectum,"* said seeds having been planted and grown by me on property under my control and supervision at Princeton, New Jersey. The original seeds from which the new seedling was ultimately selected in a nursery row of transplanted seedlings, resulted from open pollination of the parent columnar Norway maple tree, and the selection of the new variety was made by reason of the distinctive characteristics that were evident therein and which represent a new and improved combination of characteristics never previously exhibited in any maple tree of which I am aware.

The principal outstanding characteristics of my new variety by which it is definitely differentiated from the columnar Norway maple tree referred to above, and from all other varieties, are as follows:

(1) An extremely rapid, vigorous and upright habit of growth, accompanied by an excurrent habit of branching, as evidenced by its central stem or leader which extends upward through the center of the tree;

(2) A tall, ovate crown which is taller than that typical of most Norway maples which customarily have a round or global crown;

(3) A habit of developing numerous branchlets on the sides of the current growth throughout the growing season, with a resultant heavier and denser branch formation within the crown, which is especially evident in the young trees, and enables the yearling trees to be considered as branched trees, rather than merely "whips" as in the case of regular Norway maples;

(4) An extremely strong and straight trunk, which eliminates the necessity of expensive staking, said trunk having a bark color slightly lighter than that of the ordinary Norway maple;

(5) Very large, thick and more leathery foliage than that of ordinary Norway maples, said foliage being retained from 10 to 14 days longer in the fall than the foliage of most Norway maples, and turning a clear yellow color, with green veins, in the late fall, unlike other Norway maples;

(6) Considerably greater resistance to marginal leaf scorch and leaf hopper injury, the latter being extremely important to the production of Norway maple trees in the eastern part of the U. S.; and (7) New soft tip growth of light green color and without the usual reddish color which is characteristic of ordinary Norway maples.

Asexual reproduction of my new variety by budding, as performed at Princeton, New Jersey, shows that the foregoing characteristics and distinctions come true to form and are established and transmitted through succeeding propagations.

The accompanying drawing shows a typical tree of my new variety, as well as typical specimens of the foliage on a somewhat enlarged scale as it appears in observing both the upper and under surfaces thereof, all as depicted in color as nearly true as it is reasonably possible to make the same in a color illustration of this character.

The following is a detailed description of my new variety, with color terminology in accordance with the Munsell Book of Color, except where general color terms of ordinary dictionary significance are obvious:

Parentage: An open pollinated seedling of *Acer platanoides erectum.*

Propagation: Holds its distinguishing characteristics through succeeding propagations by budding (sometimes termed "bud-grafting").

Locality where grown and observed: Princeton, New Jersey.

Tree: Large; very vigorous; upright; tall; with an ovate crown; rapid-growing; hardy; medium productive (fruits lightly); regular annual bearer.

*Trunk.*—Stocky; medium smooth; very straight; naturally maintains a leader up to the top of the tree. Bark: color—slightly lighter than that of ordinary Norway maples.

*Head.*—Even; ovate (not round like an apple tree as is customary in ordinary Norway maples).

*Branches.*—Thick; smooth; excurrent habit (not deliquescent as in ordinary Norway maples); form strong crotches which are resistant to ice and wind damage.

Foliage:

*Leaves.*—Large; wide (about 23 cm.); medium length (about 15 cm.); palmately lobed (5 major lobes and from 15 to 17 minor lobes); lobes acuminate and remotely sinuate-dentate, with taper-pointed teeth; more thick and leathery than ordinary maples; remain on the tree from 10 to 14 days longer than ordinary Norway maples in the fall. Upper surface—smooth; dull; color: Dark Green, Plate 7.5 GY 3/4. Under surface—smooth; lustrous; with small tufts of brown pubescence in the axils of the veins; color: Yellow Green, Plate 5.0 GY 4/4. Margin—remotely sinuate-dentate (not glandular). Petiole—long (from about 16 to 20 cm.); medium thickness; has milky juice.

Flowers: Arranged in terminal stalked corymbs on short, leafy branchlets with from 15 to 18 flowers per corymb.

*Blooming season.*—Medium, as compared with other varieties. First bloom (in New Jersey)—about April 15th. Full bloom (in New Jersey)—about April 30th.

*Color.*—Greenish Yellow, Plate 2.5 GY 8/10.

*Size.*—From 8 to 10 mm. in diameter.

Fruit: Borne in pendulous clusters of from 12 to 15 pairs of sameras per cluster; matures in New Jersey about October 15th and fruit drops about November 5th.

*Size.*—From about 8.5 to about 9.5 cm. across pair of sameras. Individual samera size: length overall—about 48 mm.; length of wing—about 36 mm.; length of nutlet—about 12 mm.; width of wing—about 12 mm.; width of nutlet—about 9 mm.

*Color* (*Mature sameras*).—Wing—Light Yellowish Brown, Plate 2.5 Y 7/6. Nutlet—Reddish Brown, Plate 2.5 YR 3/6.

Insert Resistance: Excellent; has proved highly resistant to the toxic effects of leaf hopper (*Empoasca fabae*) feeding; trees continued to grow vigorously under heavy infestation when other varieties in the same row or block were so severely injured as to cease growth and form small terminal rosettes of leaves, as noted from extended observation at Princeton, New Jersey.

Disease Resistance: Good; has proved resistant to Verticillium wilt disease in the same blocks where other varieties showed considerable mortality due to this fungus disease, as noted from prolonged observation at Princeton, New Jersey.

I claim:

A new and distinct variety of Norway maple tree, substantially as herein shown and described, characterized particularly as to novelty by a unique combination of its extremely rapid, vigorous and upright habit of growth, accompanied by an excurrent habit of branching as evidenced by its central stem or leader which extends upward through the center of the tree, its tall, ovate crown which is taller than that typical of most Norway maples, a habit of developing numerous branchlets on the sides of the current growth throughout the growing season with a resultant heavy and dense branch formation within the crown which is particularly evident in the young trees, its extremely strong and straight trunk which has a bark of slightly lighter color than that of ordinary Norway maples, its very large, thick and leathery foliage which is retained from 10 to 14 days longer in the fall than that of other Norway maples, and which turn a clear yellow color, with green veins in the late fall, its exceptionally good resistance to marginal leaf scorch and leaf hopper injury, and its new soft tip growth of light green color without the usual reddish color which is characteristic of ordinary Norway maples.

No references cited.